(12) United States Patent  
Salahieh et al.

(10) Patent No.: US 7,998,163 B2
(45) Date of Patent: Aug. 16, 2011

(54) EXPANDABLE RETRIEVAL DEVICE

(75) Inventors: Amr Salahieh, Saratoga, CA (US);
Michael Schultz, Santa Cruz, CA (US);
Paul Laduca, Buffalo, NY (US);
Thomas E. Broome, Shakopee, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1047 days.

(21) Appl. No.: 10/677,716

(22) Filed: Oct. 2, 2003

(65) Prior Publication Data
US 2004/0127936 A1 Jul. 1, 2004

Related U.S. Application Data

(60) Provisional application No. 60/415,396, filed on Oct. 2, 2002.

(51) Int. Cl.
*A61M 29/00* (2006.01)
(52) U.S. Cl. ........................................ 606/200
(58) Field of Classification Search .................. 606/200, 606/114, 113, 117; 623/1.11, 23.72; 604/103.05, 604/103.06, 103.09
See application file for complete search history.

(56) References Cited

U.S. PATENT DOCUMENTS

| | | | |
|---|---|---|---|
| 3,472,230 A | 10/1969 | Fogarty | |
| 3,592,186 A | 7/1971 | Oster | |
| 3,683,904 A | 8/1972 | Forster | |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,447,227 A | 5/1984 | Kotsanis | |
| 4,580,568 A | 4/1986 | Gianturco | |
| 4,590,938 A | 5/1986 | Segura et al. | |
| 4,619,246 A | 10/1986 | Molgaard-Nielsen et al. | |
| 4,631,052 A | 12/1986 | Kensey | |
| 4,643,184 A | 2/1987 | Mobin-Uddin | |
| 4,650,466 A | 3/1987 | Luther | |
| 4,662,885 A | 5/1987 | DiPisa, Jr. | |
| 4,705,517 A | 11/1987 | DiPisa, Jr. | |
| 4,706,671 A | 11/1987 | Weinrib | |
| 4,723,549 A | 2/1988 | Wholey et al. | |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner* — Melanie Tyson
(74) *Attorney, Agent, or Firm* — Seager, Tufte & Wickhem LLC

(57) ABSTRACT

A device for retrieving an intravascular device from a body lumen is disclosed. A retrieval device in accordance with an exemplary embodiment of the present invention includes a braided member coupled to an elongated shaft member. The braided member may include a number of filaments defining a radially expandable inner lumen configured to receive and encapsulate the intravascular device therein. An elastomeric jacket disposed about at least a portion of the braided member may encase the filaments.

25 Claims, 4 Drawing Sheets

U.S. PATENT DOCUMENTS

| | | | |
|---|---|---|---|
| 4,728,319 A | 3/1988 | Masch | |
| 4,733,665 A | 3/1988 | Palmaz | |
| 4,790,812 A | 12/1988 | Hawkins, Jr. et al. | |
| 4,790,813 A | 12/1988 | Kensey | |
| 4,794,928 A | 1/1989 | Kletschka | |
| 4,794,931 A | 1/1989 | Yock | |
| 4,800,882 A | 1/1989 | Gianturco | |
| 4,807,626 A | 2/1989 | McGirr | |
| 4,842,579 A | 6/1989 | Shiber | |
| 4,857,045 A | 8/1989 | Rydell | |
| 4,857,046 A | 8/1989 | Stevens et al. | |
| 4,867,157 A | 9/1989 | McGurk-Burleson et al. | |
| 4,873,978 A | 10/1989 | Ginsburg | |
| 4,886,061 A | 12/1989 | Fischelle et al. | |
| 4,898,575 A | 2/1990 | Fischell et al. | |
| 4,907,336 A | 3/1990 | Gianturco | |
| 4,921,478 A | 5/1990 | Solano et al. | |
| 4,921,484 A | 5/1990 | Hillstead | |
| 4,926,858 A | 5/1990 | Gifford, III et al. | |
| 4,950,277 A | 8/1990 | Farr | |
| 4,955,895 A | 9/1990 | Sugiyama et al. | |
| 4,957,482 A | 9/1990 | Shiber | |
| 4,969,891 A | 11/1990 | Gewertz | |
| 4,979,951 A | 12/1990 | Simpson | |
| 4,986,807 A | 1/1991 | Farr | |
| 4,998,539 A | 3/1991 | Delsanti | |
| 5,002,560 A | 3/1991 | Machold et al. | |
| RE33,569 E | 4/1991 | Gifford, III et al. | |
| 5,007,896 A | 4/1991 | Shiber | |
| 5,007,917 A | 4/1991 | Evans | |
| 5,011,488 A | 4/1991 | Ginsburg | |
| 5,019,088 A | 5/1991 | Farr | |
| 5,041,126 A | 8/1991 | Gianturco | |
| 5,053,008 A | 10/1991 | Bajaj | |
| 5,053,044 A | 10/1991 | Mueller et al. | |
| 5,071,407 A | 12/1991 | Termin et al. | |
| 5,071,425 A | 12/1991 | Gifford, III et al. | |
| 5,085,662 A | 2/1992 | Willard | |
| 5,087,265 A | 2/1992 | Summers | |
| 5,100,423 A | 3/1992 | Fearnot | |
| 5,100,424 A | 3/1992 | Jang et al. | |
| 5,100,425 A | 3/1992 | Fischell et al. | |
| 5,102,415 A | 4/1992 | Guenther et al. | |
| 5,104,399 A | 4/1992 | Lazarus | |
| 5,108,419 A | 4/1992 | Reger et al. | |
| 5,133,733 A | 7/1992 | Rasmussen et al. | |
| 5,135,531 A | 8/1992 | Shiber | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,171,233 A | 12/1992 | Amplatz et al. | |
| 5,190,546 A | 3/1993 | Jervis | |
| 5,195,955 A | 3/1993 | Don | |
| 5,221,261 A | 6/1993 | Termin et al. | |
| 5,224,953 A | 7/1993 | Morgentaler | |
| 5,306,286 A | 4/1994 | Stack et al. | |
| 5,314,444 A | 5/1994 | Gianturco | |
| 5,314,472 A | 5/1994 | Fontaine | |
| 5,318,576 A | 6/1994 | Plassche, Jr. et al. | |
| 5,329,942 A | 7/1994 | Gunther et al. | |
| 5,330,484 A | 7/1994 | Gunther | |
| 5,330,500 A | 7/1994 | Song | |
| 5,350,398 A | 9/1994 | Pavcnik et al. | |
| 5,354,310 A | 10/1994 | Garnic et al. | |
| 5,356,423 A | 10/1994 | Tihon et al. | |
| 5,366,464 A | 11/1994 | Belknap | |
| 5,366,473 A | 11/1994 | Winston et al. | |
| 5,370,657 A | 12/1994 | Irie | |
| 5,370,683 A | 12/1994 | Fontaine | |
| 5,376,100 A | 12/1994 | Lefebvre | |
| 5,383,887 A | 1/1995 | Nadal | |
| 5,383,892 A | 1/1995 | Cardon et al. | |
| 5,383,926 A | 1/1995 | Lock et al. | |
| 5,387,235 A | 2/1995 | Chuter | |
| 5,395,349 A | 3/1995 | Quiachon et al. | |
| 5,397,345 A | 3/1995 | Lazarus | |
| 5,405,377 A | 4/1995 | Cragg | |
| 5,409,454 A | 4/1995 | Fischell et al. | |
| 5,415,630 A | 5/1995 | Gory et al. | |
| 5,419,774 A | 5/1995 | Willard et al. | |
| 5,421,832 A | 6/1995 | Lefebvre | |
| 5,423,742 A | 6/1995 | Theron | |
| 5,423,885 A | 6/1995 | Williams | |
| 5,425,765 A | 6/1995 | Tiefenbrun et al. | |
| 5,443,498 A | 8/1995 | Fontaine | |
| 5,449,372 A | 9/1995 | Schmaltz et al. | |
| 5,456,667 A | 10/1995 | Ham et al. | |
| 5,462,529 A | 10/1995 | Simpson et al. | |
| 5,476,104 A | 12/1995 | Sheahon | |
| 5,484,418 A | 1/1996 | Quiachon et al. | |
| 5,507,767 A | 4/1996 | Maeda et al. | |
| 5,512,044 A | 4/1996 | Duer | |
| 5,527,354 A | 6/1996 | Fontaine et al. | |
| 5,536,242 A | 7/1996 | Willard et al. | |
| 5,540,707 A | 7/1996 | Ressemann et al. | |
| 5,549,626 A * | 8/1996 | Miller et al. ................ 606/200 |
| 5,562,724 A | 10/1996 | Vowerk et al. | |
| 5,569,274 A | 10/1996 | Rapacki et al. | |
| 5,569,275 A | 10/1996 | Kotula et al. | |
| 5,584,821 A | 12/1996 | Hobbs et al. | |
| 5,630,822 A * | 5/1997 | Hermann et al. ............ 606/114 |
| 5,634,897 A | 6/1997 | Dance et al. | |
| 5,658,296 A | 8/1997 | Bates et al. | |
| 5,662,671 A | 9/1997 | Barbut et al. | |
| 5,669,933 A | 9/1997 | Simon et al. | |
| 5,695,519 A | 12/1997 | Summers et al. | |
| 5,709,704 A | 1/1998 | Nott et al. | |
| 5,720,764 A | 2/1998 | Naderlinger | |
| 5,728,066 A | 3/1998 | Daneshvar | |
| 5,746,758 A | 5/1998 | Nordgren et al. | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,792,300 A | 8/1998 | Inderbitzen et al. | |
| 5,795,322 A | 8/1998 | Boudewijn | |
| 5,797,952 A | 8/1998 | Klein | |
| 5,800,457 A | 9/1998 | Gelbfish | |
| 5,800,525 A | 9/1998 | Bachinski et al. | |
| 5,807,398 A | 9/1998 | Shaknovich | |
| 5,810,874 A | 9/1998 | Lefebvre | |
| 5,814,058 A * | 9/1998 | Carlson et al. ................ 606/185 |
| 5,814,064 A | 9/1998 | Daniel et al. | |
| 5,817,102 A | 10/1998 | Johnson et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,836,868 A | 11/1998 | Ressemann et al. | |
| 5,846,260 A | 12/1998 | Maahs | |
| 5,848,964 A | 12/1998 | Samuels | |
| 5,876,367 A | 3/1999 | Kaganov et al. | |
| 5,893,867 A | 4/1999 | Bagaoisan et al. | |
| 5,895,399 A | 4/1999 | Barbut et al. | |
| 5,902,263 A | 5/1999 | Patterson et al. | |
| 5,906,618 A | 5/1999 | Larson, III | |
| 5,908,435 A | 6/1999 | Samuels | |
| 5,910,154 A | 6/1999 | Tsugita et al. | |
| 5,911,734 A | 6/1999 | Tsugita et al. | |
| 5,916,193 A | 6/1999 | Stevens et al. | |
| 5,925,016 A | 7/1999 | Chornenky et al. | |
| 5,925,060 A | 7/1999 | Forber | |
| 5,925,062 A | 7/1999 | Purdy | |
| 5,925,063 A | 7/1999 | Khosravi | |
| 5,928,203 A | 7/1999 | Davey et al. | |
| 5,928,218 A | 7/1999 | Gelbfish | |
| 5,934,284 A | 8/1999 | Plaia et al. | |
| 5,935,139 A | 8/1999 | Bates | |
| 5,938,645 A | 8/1999 | Gordon | |
| 5,941,869 A | 8/1999 | Patterson et al. | |
| 5,941,896 A | 8/1999 | Kerr | |
| 5,947,995 A | 9/1999 | Samuels | |
| 5,951,585 A | 9/1999 | Cathcart et al. | |
| 5,954,745 A | 9/1999 | Gertler et al. | |
| 5,976,172 A | 11/1999 | Homsma et al. | |
| 5,980,555 A | 11/1999 | Barbut et al. | |
| 5,989,210 A | 11/1999 | Morris et al. | |
| 5,989,271 A | 11/1999 | Bonnette et al. | |

| Patent No. | Date | Inventor |
|---|---|---|
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 * | 4/2001 | Dubrul et al. .................. 600/159 |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,738 B1 * | 6/2001 | Dereume ....................... 606/108 |
| 6,245,087 B1 | 6/2001 | Addis |
| 6,245,088 B1 | 6/2001 | Lowery |
| 6,245,089 B1 * | 6/2001 | Daniel et al. ................... 606/200 |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 * | 9/2001 | Cryer et al. .................... 606/200 |
| 6,309,399 B1 | 10/2001 | Barbut et al. |
| 6,312,407 B1 | 11/2001 | Zadno-Azizi et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,344,049 B1 | 2/2002 | Levinson et al. |
| 6,346,116 B1 | 2/2002 | Brooks et al. |
| 6,364,895 B1 | 4/2002 | Greenhalgh |
| 6,375,670 B1 | 4/2002 | Greenhalgh |
| 6,383,205 B1 | 5/2002 | Samson et al. |
| 6,432,122 B1 | 8/2002 | Gilson et al. |
| 6,500,203 B1 | 12/2002 | Thompson et al. |
| 6,540,712 B1 | 4/2003 | Parodi et al. |
| 6,544,279 B1 | 4/2003 | Hopkins et al. |
| 6,589,263 B1 | 7/2003 | Hopkins et al. |
| 6,596,011 B2 | 7/2003 | Johnson et al. |
| 6,602,271 B2 | 8/2003 | Adams et al. |
| 6,623,506 B2 | 9/2003 | McGuckin, Jr. et al. |
| 7,658,747 B2 * | 2/2010 | Forde et al. .................... 606/200 |
| 2001/0051810 A1 | 12/2001 | Dubrul et al. |
| 2002/0091407 A1 * | 7/2002 | Zadno-Azizi et al. ........ 606/200 |
| 2002/0188314 A1 * | 12/2002 | Anderson et al. ............. 606/200 |
| 2003/0004537 A1 * | 1/2003 | Boyle et al. ................... 606/200 |

FOREIGN PATENT DOCUMENTS

| | | |
|---|---|---|
| DE | 34 17 738 | 11/1985 |
| DE | 40 30 998 A1 | 10/1990 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 | 5/1979 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/04875 A1 | 2/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |

OTHER PUBLICATIONS

"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).

Cragg, Andrew et al., "A New *Percutaneous vena Cava* Filger," *AJR*, 141:601-604, (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery* 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 1994.

Moussa, MD, Issaam "Stents Don't Require Systemic Anticoagulation . . . But the Technique (and Results) Must be Optimal," *Journal of Invasive Cardiol.*, 8(E):3E-7E, 1996.

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

\* cited by examiner

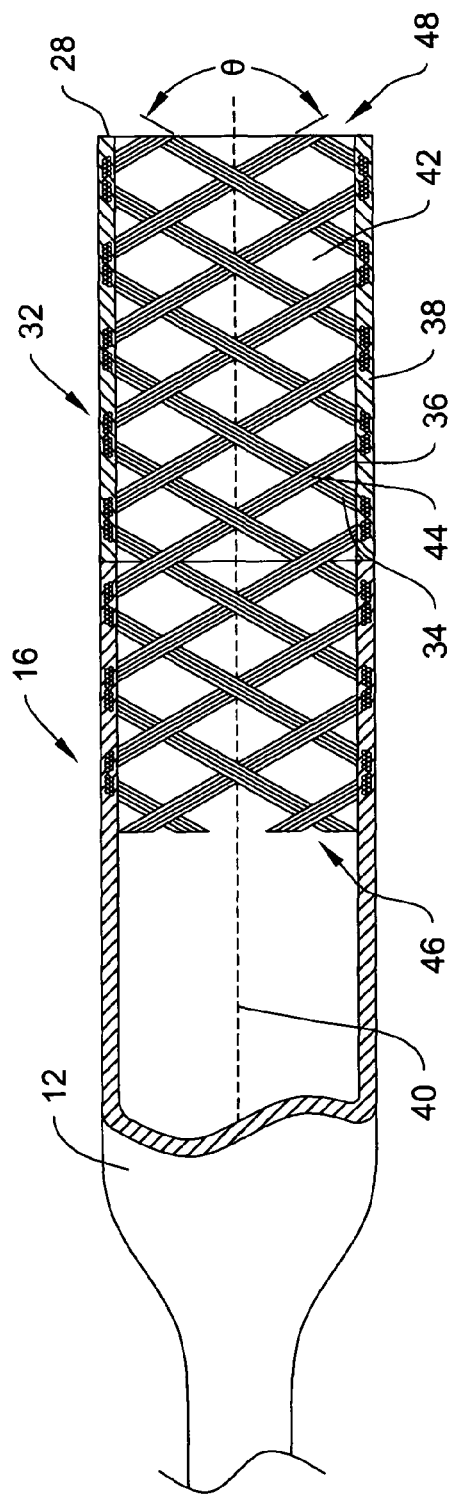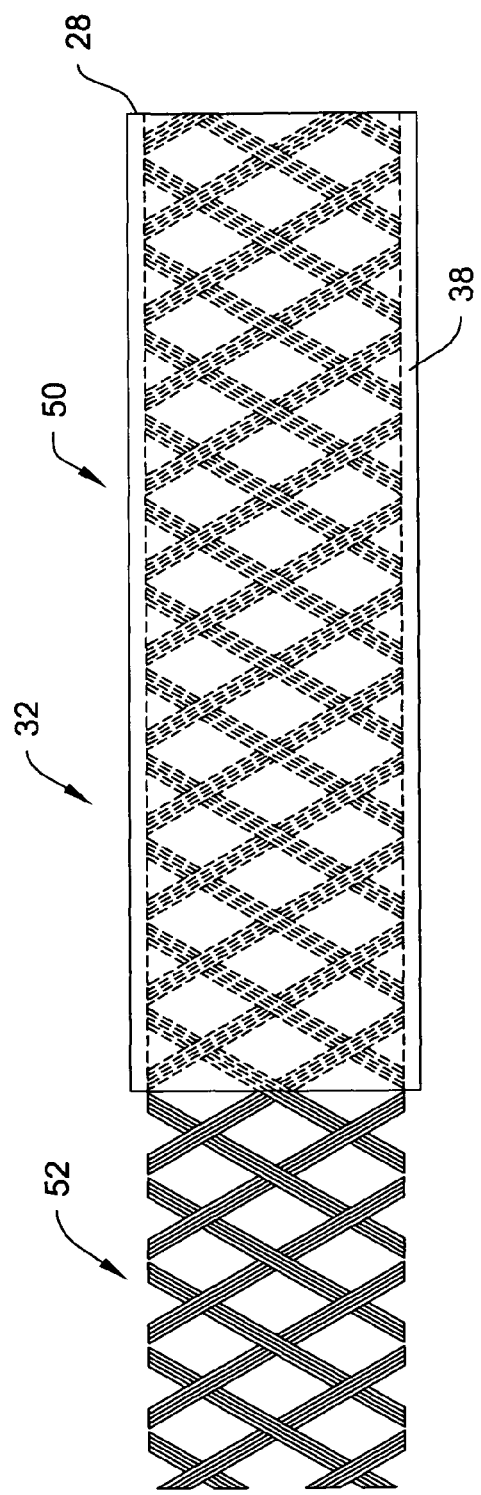

EXPANDABLE RETRIEVAL DEVICE

CROSS REFERENCE TO RELATED APPLICATION

The present application claims benefit to provisional U.S. Patent Application No. 60/415,396, filed on Oct. 2, 2002.

FIELD OF THE INVENTION

The present invention relates generally to the field of intravascular devices. More specifically, the present invention pertains to retrieval devices for embolic protection filters.

BACKGROUND OF THE INVENTION

Intravascular devices such as an embolic protection filters are typically placed in a vessel such as an artery or vein to filter emboli contained in the blood stream. Examples of procedures employing such filters include angioplasty, atherectomy, thrombectomy, and stenting. These procedures generally involve transluminally inserting and delivering within the artery or vein an elongated wire and filter to a location distal a lesion. Once placed, a therapeutic device such as an angioplasty catheter is advanced along the wire to the site of the lesion to perform a therapeutic procedure (e.g. percutaneous transluminal coronary angioplasty). A stent can also be advanced to the site of the lesion and engaged along the wall of the vessel to prevent restenosis from occurring within the vessel.

Retrieval of the embolic protection filter generally involves the use of a catheter or sheath having an inner lumen configured to collapse the filter and captured emboli therein. The ability of such retrieval devices to effectively trap the filter and its contents may depend in part on the size of the filter and filter wire, and the amount of emboli collected. The profile of the catheter or sheath may also affect the ability of the retrieval device to be delivered through the body.

SUMMARY OF THE INVENTION

The present invention pertains to retrieval devices for embolic protection filters. A retrieval device in accordance with an exemplary embodiment of the present invention includes an elongated shaft member having a proximal section, a distal section, and an inner lumen therethrough. A braided member coupled to the distal section of the elongated shaft member may be configured to receive and encapsulate an embolic protection filter therein. The braided member may include a number of filaments configured to radially expand when axially compressed. An elastomeric jacket disposed about at least a portion of the braided member may be used to encase the filaments. Methods of forming and using such devices are also disclosed.

BRIEF DESCRIPTION OF THE DRAWINGS

FIG. 2 is a fragmentary cross-sectional view of a distal portion of the retrieval device of FIG. 1;

FIG. 3 is a perspective view of a braided member used in the construction of the retrieval device of FIG. 1;

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
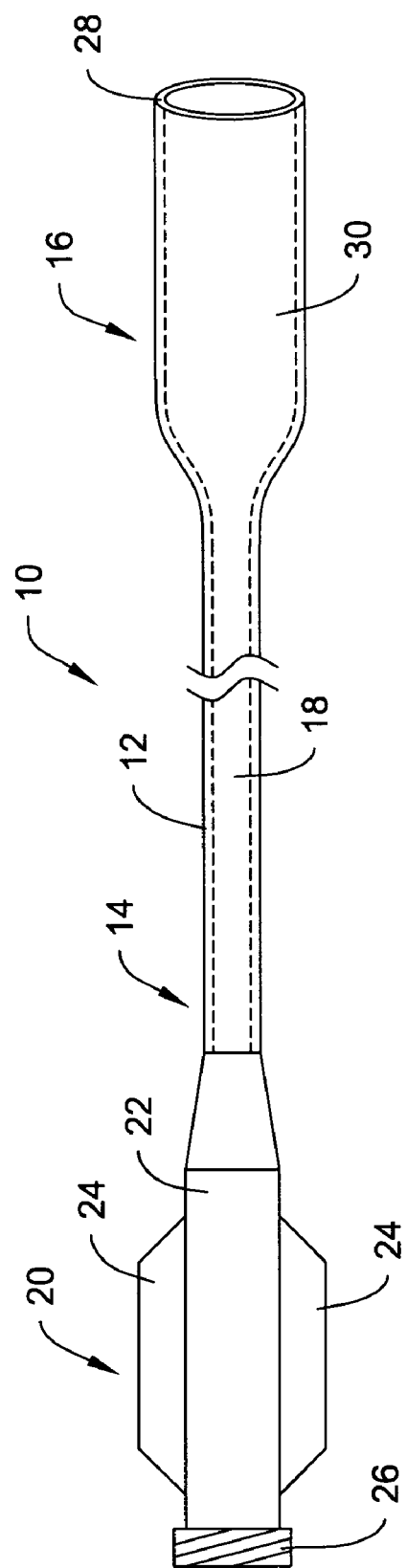
FIG. 1 is a perspective view of a retrieval device in accordance with an exemplary embodiment of the present invention.

FIG. 1 is a perspective view of a retrieval device 10 in accordance with an exemplary embodiment of the present invention. Retrieval device 10 includes an elongated shaft member 12 having a proximal section 14, a distal section 16, and an inner lumen 18 therethrough. The elongated shaft member 12 may include a suitably stiff material having sufficient column strength and rigidity to withstand buckling as the retrieval device 10 is advanced over an intravascular device such as an embolic protection filter. The wall thickness of the elongated shaft member 12 may be generally uniform along the length of the retrieval device 10, or may vary to alter the flexibility or bending characteristics of the device 10, as desired. Materials suitable for forming the elongated shaft member 12 include polymers such as polyether block amide (PEBA), or metal-polymer blends such as stainless steel reinforced hypotube. Polyether block amide (PEBA) is commercially available from Atochem Polymers of Birdsboro, Pa. under the trade name PEBAX.

The proximal section 14 of the elongated shaft member 12 may be provided with a hub 20 having a handle 22 and a number of gripping fins 24 that allow the user to grip the proximal section 14 and manipulate the retrieval device 10 both axially and rotationally within the body. In certain embodiments, a vacuum source 26 coupled to the hub 20 and in fluid communication with the inner lumen 18 may be used to provide suction at the distal end 28 of the retrieval device 10. In use, the vacuum source 26 may be used to aspirate the embolic protection filter and any loose emboli into the retrieval device 10. Such suction force can be used in lieu of, or in addition to, manually manipulating the retrieval device 10 within the body to retrieve the intravascular device.

The distal section 16 of the elongated shaft member 12 may be flared slightly, forming a retrieval lumen 30 configured to expand and encapsulate the intravascular device therein. A braided member 32 (FIG. 2) coupled to or formed integrally with the distal section 16 may be utilized to impart flexibility to the distal portion of the retrieval device 10 while maintaining the axial stiffness and rigidity characteristics generally exhibited by the remainder of the elongated shaft member 12.

FIG. 2 is a fragmentary cross-sectional view of a distal portion of the retrieval device 10 of FIG. 1. Braided member 32 may include a number of filaments 34,36 encased within an elastomeric jacket 38 that can be configured to lie adjacent and flush with the distal section 16 of the elongated shaft member 12. As shown in FIG. 2, at least a portion of the braided member 32 may be encased within a wall of the flared distal section 16 of the elongated shaft member 12. Elastomeric jacket 38 may have a thickness generally equivalent to that of the flared distal section 16 of the elongated shaft member 12. The filaments 34,36 may be arranged generally in two sets of parallel helices wound in opposite directions about a common longitudinal axis 40, thus forming an inner lumen 42 of the braided member 32. The filaments 34,36 may intersect each other in an overlapping pattern at a number of interstices 44. The interstices 44 are configured to permit the two sets of filaments 34,36 to move with respect to each other, allowing the braided member 32 to radially expand and axially shorten when subjected to a compressive force, and conversely, radially shrink and axially elongate when subjected to a tensile force. The braid angle θ (i.e. the angle between two filaments in the longitudinal or axial direction) may be varied to alter the amount of radial expansion and axial elongation of the braided member 32, as desired. The ends 46,48 of each of the two sets of filaments 34,36 may be constrained to prevent the filaments 34,36 from fraying or unraveling.

The shape, thickness, or other characteristics of the braided member 32 may also vary to alter the characteristics of the retrieval device 10. In the exemplary embodiment depicted in FIG. 1, the filaments 34,36 forming the braided member 32 are each made from multi-filar threads woven together to form filaments having a generally round shape. Other filament configurations may be employed, however, such as round wire, flat ribbon, threads, fibers, mono-filament, multi-filament, or combinations thereof. The thickness of the filaments 34,36 may vary in dimension to impart a greater or lesser amount of resistance to radial expansion to the braided member 32 as the intravascular device is loaded into the retrieval device 10. In general, the larger the size of filaments employed, the greater the resistance to radial expansion that results.

The expandability of the retrieval device 10 may also be due in part to the material composition of the braided member 32. The braided member 32 may comprise any number of suitable materials, including polymers, metals, metal alloys, metal-polymer composites, or metal-metal composites. Elastomeric materials may also be employed to impart a desired amount of flexibility to the braided member 32. Examples of suitable polymeric materials include, but are not limited to, polyethylene terapthalate (PET), polytetraflouroethylene (PTFE), polyurethane (Nylon) fluorinated ethylene propylene (FEP), ethylene tetrafluoroethylene (ETFE), polyurethane, polypropylene (PP), polyvinylchloride (PVC), polyether-ester, polyester, polyamide, elastomeric polyamides, block polyamide/ethers, polyether block amide (PEBA), silicones, polyethylene (PE), polyether-ether ketone (PEEK), polyimide (PI), polyetherimide (PEI), polyphenylene sulfide (PPS), polyphenylene oxide (PPO), polysulfone, perfluoro (propyl vinyl ether) (PFA), or other suitable materials, mixtures, combinations or copolymers thereof. Examples of suitable metals or metal alloys may include stainless steel, platinum, tungsten alloy and nickel-titanium alloy.

In certain embodiments, the filaments 34,36 may each be formed from a composite material configured to impart a desired characteristic to the braided member 32. For example, one or more stainless steel and nickel-titanium alloy wires can be wound together to form filaments having a desired characteristic such as superelasticity. Alternatively, in those embodiments employing wire or flat ribbon, for example, a composite material formed by a drawing, cladding or other suitable process may used to form filaments having a desired characteristic.

The filaments 34,36 may include a radiopaque metal such as gold, palladium, platinum, tantalum, and tungsten alloy, or may include a polymeric material loaded with a radiopaque agent such as barium sulfate ($BaSO_4$) or bismuth subcarbonate ($(BiO)_2CO_3$). Radiopaque materials are understood to be materials capable of producing a relatively bright image on a fluoroscopic monitor or other imaging device. When a radiopaque die is injected into the vessel at issue, the relatively bright image produced on the monitor can be used to determine the location of the retrieval device within the body.

FIG. 3 is a perspective view of the braided member 32 used in the construction of the retrieval device 10 of FIG. 1. As can be seen in FIG. 3, an elastomeric jacket 38 may be placed about a distal section 50 of the braided member 32. The proximal section 52 of the braided member 32 may, in turn, be exposed to facilitate bonding of braided member 32 to the distal section 16 of the elongated shaft member 12.

In use, the elastomeric jacket 38 constrains and compresses the filaments 34,36 radially such that the braided member 32 assumes a generally low profile for delivery through the body. In addition, the elastomeric jacket 38 protects against the intrusion of other objects between the interstices 44 of the filaments 34,36. In some embodiments, the elastomeric jacket 38 may be loaded with a radiopaque additive (e.g. barium sulfate or bismuth subcarbonate) to further enhance the visibility of the braided member 32 under a fluoroscope.

The elastomeric jacket 38 may be formed of silicon, C-flex, urethane or other suitable material having sufficient elasticity to permit the braided member 32 to radially expand while maintaining axial stiffness and rigidity. To form the elastomeric jacket 38, an uncured elastomeric material may be placed in either liquid or thixotropic form over the distal section 50 of the braided member 32. The braided member 32 is then placed in a mold while the elastomeric material is allowed to cure and assume its final solid form. In another exemplary embodiment, the elastomeric jacket 38 may be formed by an extrusion process wherein the elastomeric material is extruded or poured over the distal section 50 of the braided member 32, and then allowed to cool to its final solid form. In yet another alternative embodiment, an injection-mold process such as insert molding may be employed to bond the elastomeric jacket 38 to the braided member 32.

The braided member 32 may be formed from a separate member that is attached to the distal section 16 of the elongated shaft member 12, or may be formed integral with the elongated shaft member 12. The braided member 32 can be attached to the elongated shaft member 12 using any number of suitable bonding techniques such as adhesion, laser welding, rf welding, soldering, or crimping. In one exemplary bonding technique, a thin piece of heat-shrinking tube can be placed about the distal section 16 of elongated shaft member 12 and the braided member 32, and then heated until the two members 12,32 meld together. The heat-shrink tube can then be removed from the retrieval device 10.

Figure 4:
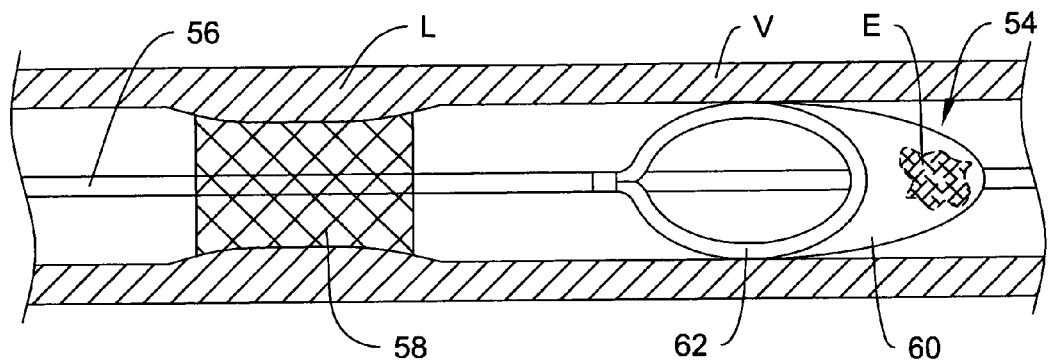
FIG. 4 is a plan view of an embolic protection filter disposed within a vessel distal a lesion and placed stent.

Referring now to FIGS. 4-9, an exemplary method of retrieving an intravascular device in accordance with the present invention will now be discussed with respect to retrieval device 10 described herein. In a first position depicted in FIG. 4, an embolic protection filter 54 attached to a filter wire 56 is shown positioned within a vessel V distal a lesion L. A previously placed stent 58 is also shown advanced along the filter wire 56 and positioned across the site of the lesion L to prevent restenosis from occurring subsequent to a therapeutic procedure such as an angioplasty or atherectomy. As can be seen in FIG. 4, the embolic protection filter 54 may include a filter mesh or membrane 60 operatively coupled to a proximal support hoop 62, which is biased to expand the filter mesh or membrane 60 within the vessel V. Throughout the course of treatment, embolic debris E dislodged from the vessel wall enters the embolic protection filter 54 through the proximal support hoop 62, where it is collected and stored within the filter mesh or membrane 60.

Figure 5:
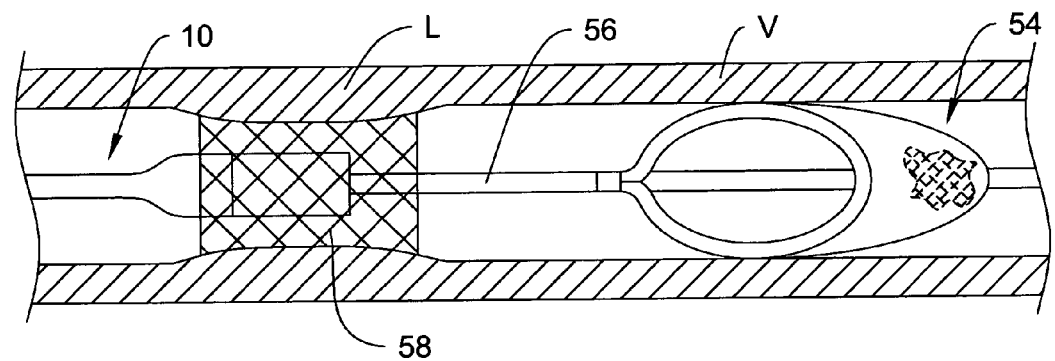
FIG. 5 is another plan view of the vessel shown in FIG. 4, wherein a retrieval device is shown advanced along the filter wire.

At the conclusion of the therapeutic procedure, the retrieval device 10 can be advanced along the filter wire 56 across the site of the lesion L, as shown in FIG. 5. During delivery, the retrieval device 10 assumes a relatively low profile, allowing the device to be advanced through the stent 58 with minimal interference.

Figure 6:
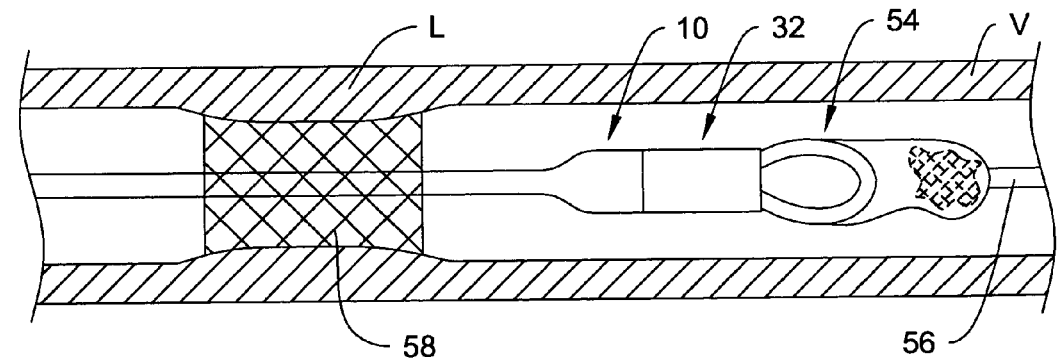
FIG. 6 is another plan view of the vessel shown in FIG. 4, wherein the retrieval device has been further advanced along the filter wire to collapse the filter.
Figure 7:
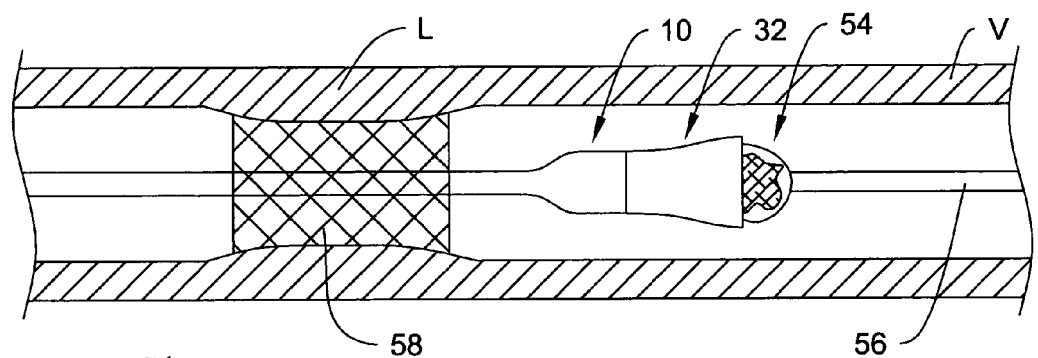
FIG. 7 is another plan view of the vessel shown in FIG. 4, wherein the filter is partially collapsed within the retrieval device.
Figure 8:
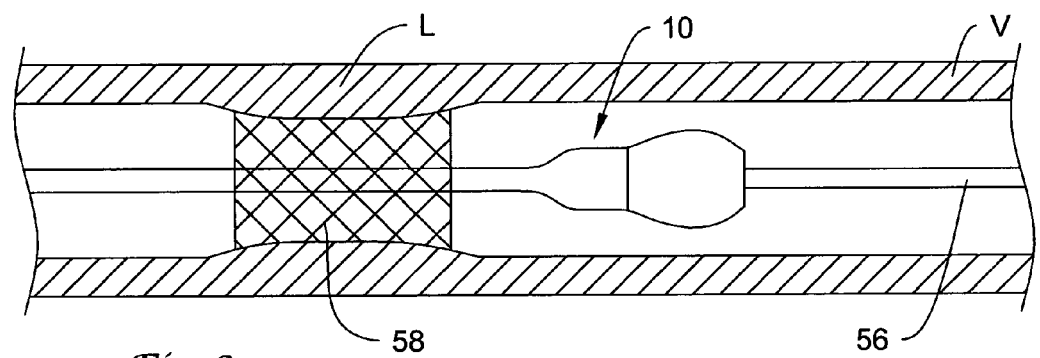
FIG. 8 is another plan view of the vessel shown in FIG. 4, wherein the filter is fully encapsulated within the retrieval device.
Figure 9:
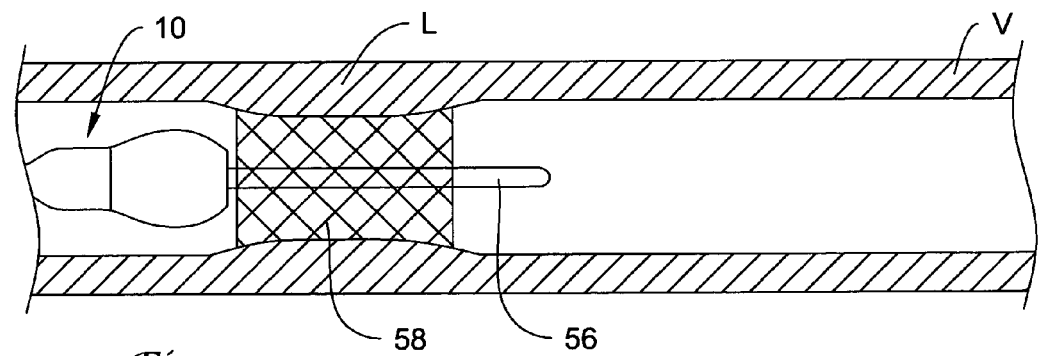
FIG. 9 is another plan view of the vessel shown in FIG. 4, wherein the retrieval device and encapsulated filter are withdrawn proximal the lesion and stent.

Continued advancement of the retrieval device 10 over the filter wire 56 causes the embolic protection filter 54 to begin to collapse within the braided member 32, as shown in FIG. 6. As the embolic protection filter 54 is further forced therein, the braided member 32 compresses axially and expands radially, as shown in FIG. 7. A suction force may also be applied to the distal end 28 of the retrieval device 10 to aspirate the embolic protection filter 54 and its contents therein. The embolic protection filter 54 and captured emboli E can then be completely encapsulated within the retrieval device 10, as shown in FIG. 8. Subsequently, the retrieval device 10, embolic protection filter 54, and captured emboli E can then be removed from the vessel V along with the filter wire 56, as shown in FIG. 9.

While FIGS. 4-9 illustrate the removal of an embolic protection filter from the body, it is contemplated that any number of other intravascular devices may be retrieved and/or delivered with the present invention. Examples of other intravascular devices may include stents, clot pullers, vena cava filters, atheterectomy devices, angioplasty devices, or the like.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention as described in the appended claims.

What is claimed is:

1. A medical device for retrieving an intravascular device from a body lumen, comprising:
    an elongated shaft member having a proximal section and a flared distal section; and
    a braided member having a proximal portion and a distal portion, the proximal portion of the braided member extending proximally of a distal end of the elongated shaft member and coupled to the flared distal section of the elongated shaft member, and the distal portion of the braided member extending distally of the distal end of the elongated shaft member, the braided member including a plurality of filaments and defining a radially expandable inner lumen configured to receive and encapsulate the intravascular device therein;
    wherein said plurality of filaments are configured to radially expand when axially compressed;
    wherein at least part of the proximal portion of the braided member is encased within a wall of the flared distal section;
    wherein the medical device is adapted to retrieve an embolic protection filter including a filter membrane coupled to a proximal support hoop, the support hoop defining a proximally facing opening of the embolic protection filter, the embolic protection filter having a first position, wherein the proximally facing opening is distal of the braided member, and a second position, wherein the proximally facing opening is within at least a portion of the radially expandable inner lumen of the braided member.

2. The medical device of claim 1, wherein the elongated shaft member includes polyether block amide.

3. The medical device of claim 1, wherein said plurality of filaments are arranged in two sets of parallel helices wound in opposite directions about a common longitudinal axis.

4. The medical device of claim 1, wherein said plurality of filaments comprise multi-filar threads.

5. The medical device of claim 1, wherein said plurality of filaments comprise a composite material.

6. The medical device of claim 5, wherein said composite material includes a radiopaque material.

7. The medical device of claim 1, wherein said plurality of filaments comprise a polymeric material.

8. The medical device of claim 1, wherein said plurality of filaments comprise a metal.

9. The medical device of claim 1, further comprising an elastomeric jacket encasing at least part of said braided member.

10. The medical device of claim 9, wherein said elastomeric jacket includes silicone.

11. The medical device of claim 9, wherein said elastomeric jacket includes urethane.

12. The medical device of claim 9, wherein said elastomeric jacket includes a radiopaque material.

13. A medical device for retrieving an intravascular device from a body lumen, comprising:
    an elongated shaft member having a proximal section and a flared distal section;
    a braided member having a proximal portion and a distal portion, the proximal portion of the braided member extending proximally of a distal end of the elongated shaft member and coupled to the flared distal section of the elongated shaft member, and the distal portion of the braided member extending distally of the distal end of the elongated shaft member, the braided member including plurality of filaments and defining a radially expandable inner lumen configured to receive and encapsulate the intravascular device therein; and
    an elastomeric jacket encasing at least part of said braided member;
    wherein at least part of the proximal portion of the braided member is integrally formed with the elongated shaft member such that the at least part of the proximal portion member is encased within a wall of the flared distal section;
    wherein the medical device is adapted to retrieve an embolic protection filter including a filter membrane coupled to a proximal support hoop, the support hoop defining a proximally facing opening of the embolic protection filter, the embolic protection filter having a first position, wherein the proximally facing opening is distal of the braided member, and a second position, wherein the proximally facing opening is within at least a portion of the radially expandable inner lumen of the braided member.

14. The medical device of claim 13, wherein the elongated shaft member includes polyether block amide.

15. The medical device of claim 13, wherein said plurality of filaments are arranged in two sets of parallel helices wound in opposite directions about a common longitudinal axis.

16. The medical device of claim 13, wherein said plurality of filaments are configured to radially expand when axially compressed.

17. The medical device of claim 13, wherein said plurality of filaments comprise multi-filar threads.

18. The medical device of claim 13, wherein said plurality of filaments comprise a composite material.

19. The medical device of claim 18, wherein said composite material includes a radiopaque material.

20. The medical device of claim 13, wherein said plurality of filaments comprise a polymeric material.

21. The medical device of claim 13, wherein said plurality of filaments comprise a metal.

22. The medical device of claim 13, wherein said elastomeric jacket includes silicone.

23. The medical device of claim 13, wherein said elastomeric jacket includes urethane.

24. The medical device of claim 13, wherein said elastomeric jacket includes a radiopaque material.

25. A medical device for retrieving an intravascular device from a body lumen, comprising:
   an elongated shaft member having a proximal section and a flared distal section;
   a braided member having a proximal portion and a distal portion, the proximal portion of the braided member extending proximally of a distal end of the elongated shaft member and fixedly coupled to the flared distal section of the elongated shaft member, and the distal portion of the braided member extending distally of the distal end of the elongated shaft member, the braided member including plurality of filaments arranged in two sets of parallel helices wound in opposite directions about a common longitudinal axis and defining a radially expandable inner lumen configured to receive and encapsulate the intravascular device therein;
   wherein at least part of the proximal portion of the braided member is integrally formed with the elongated shaft member such that the at least part of the proximal portion is encased within a wall of the flared distal section; and
   an elastomeric jacket encasing at least part of said braided member, the elastomeric jacket disposed adjacent and flush with the flared distal section of the elongated shaft member, wherein the elastomeric jacket has a thickness generally equivalent to that of the flared distal section of the elongated shaft member;
   wherein the plurality of filaments are configured to radially expand when axially compressed;
   wherein the medical device is adapted to retrieve an embolic protection filter including a filter membrane coupled to a proximal support hoop, the support hoop defining a proximally facing opening of the embolic protection filter, the embolic protection filter having a first position, wherein the proximally facing opening is distal of the braided member, and a second position, wherein the proximally facing opening is within at least a portion of the radially expandable inner lumen of the braided member.

* * * * *